Figure 1:
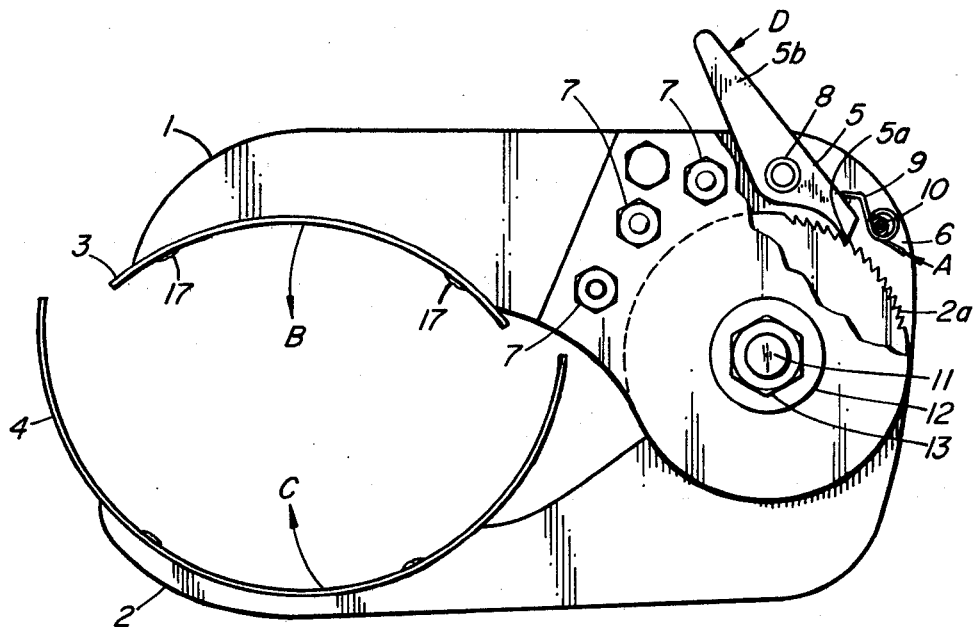

United States Patent [19]

Dyck et al.

[11] Patent Number: 4,466,437
[45] Date of Patent: Aug. 21, 1984

[54] CLAMPING DEVICE

[75] Inventors: Walter Dyck, Medicine Hat; Bernard J. Wenner, Ralston; Walter J. Fenrick, Medicine Hat, all of Canada

[73] Assignee: Her Majesty the Queen in right of Canada, as represented by the Minister of National Defence, Ottawa, Canada

[21] Appl. No.: 396,129

[22] Filed: Jul. 7, 1982

[30] Foreign Application Priority Data

Nov. 10, 1981 [CA] Canada .................................. 390094

[51] Int. Cl.³ .......................... A61B 17/12; B25B 7/14
[52] U.S. Cl. ..................................... 128/327; 128/346; 81/338
[58] Field of Search .................... 24/24, 248 B, 249 R; 248/316.7; 292/258; 81/337, 338, 420; 128/327, 346

[56] References Cited

U.S. PATENT DOCUMENTS

| | | | |
|---|---|---|---|
| 838,514 | 12/1906 | Baker | 81/338 X |
| 1,635,137 | 7/1927 | Mullens | 128/346 |
| 2,567,182 | 9/1951 | Cohen | 128/327 |
| 2,577,008 | 12/1951 | Engstrom | 128/327 |
| 2,861,574 | 11/1958 | Braslow | 128/327 |
| 4,223,673 | 9/1980 | Harris | 128/327 X |
| 4,300,573 | 11/1981 | Rebbe et al. | 128/327 X |

Primary Examiner—Robert P. Swiatek
Attorney, Agent, or Firm—Stevens, Davis, Miller & Mosher

[57] ABSTRACT

The invention disclosed is a clamping device, particularly for use in conjunction with a conventional sphygmomanometer cuff and electronic stethoscope in order to obtain a blood pressure reading from a patient's arm through heavy overgarments or the like, the patient's arm not being directly accessible. The clamping device includes a pair of pivoting jaws each carrying pressure plates for exerting pressure on the patient's arm. The sphygmomanometer cuff is placed against the patient's arm over the overgarment and the clamping device holds the cuff firmly against the arm. A releaseable lock serves to maintain the clamping device in a working position.

3 Claims, 2 Drawing Figures

CLAMPING DEVICE

This invention relates to a clamping device, particularly for use in combination with a conventional sphygmomanometer (blood pressure measuring) apparatus.

There are basically two methods of measuring blood pressure, the direct and the indirect method. The direct method involves catheterization of a major artery and taking direct and continuous readings of pressure, usually in a clinical environment. This method, however, is impratical in a field scenario. The indirect method requires a device called a sphygmomanometer which is found in almost every medical kit. An inflatable cuff, connected to a mercury manometer, is wrapped around the upper arm and the pressure in the cuff is raised to a point well above the systolic blood pressure. A stethoscope is placed over the brachial artery just below the lower edge of the cuff and the cuff is allowed to deflate slowly. The appearance, followed by the disappearance of the Korotkow sounds indicates systolic and diastolic blood pressure respectively. This method is widely used in the field but does require a cuff be placed around the upper arm.

The problem being addressed here is the case when the cuff cannot be placed around the arm. This case become more prevalent when considering non-conventional warfare, because of the protective clothing worn, or protective devices a casualty is placed into. An example of such a case occurs when a casualty is in a casualty bag and the bag cannot be opened because by doing so, the casualty may be exposed to further risk if still within a toxic environment.

The underlying principle in taking blood pressure is the ability to occlude an artery using a known pressure. Therefore, it is not necessary to wrap something (like a cuff) around the arm as long as enough pressure can be exerted against the artery to occlude it.

It is thus an object of this invention to permit the taking of blood pressures when a patient's arm is not directly accessible It is another object of this invention to provide a clamping device which can be used in conjunction with a standard sphygmomanometer and an electronic stethoscope to provide a blood pressure reading when the patient's arm is not directly accessible. An electronic stethoscope such as the one described in applicant's co-pending Canadian application Ser. No. 350,599 may be employed.

According to the invention, a clamping device for exerting pressure on an object is contemplated, comprising a pair of jaws; pivot means to permit relative pivotal movement of said pair of jaws; releasable locking means associated with said pivot means to lock said pair of jaws in a working position; and pressure plate means carried by each of said pair of jaws for applying pressure to said object therebetween.

Figure 2:
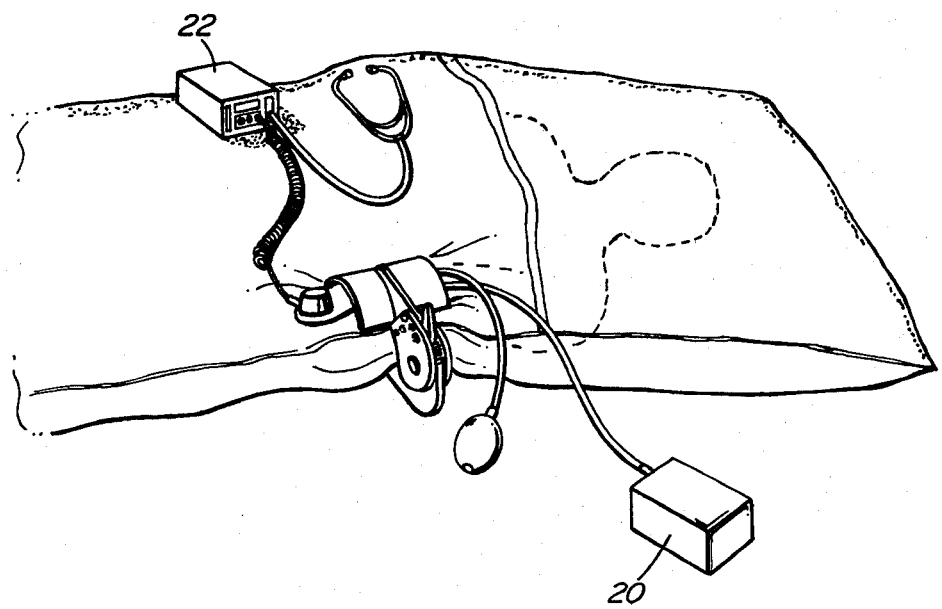

In the drawing which illustrates a preferred embodiment of the invention,

FIG. 1 is a side elevation, partly in section of a clamping device according to the invention, and FIG. 2 is a perspective view of a clamping device according to the invention in use.

Referring specifically to the drawing, the clamping device according to the invention is seen to comprise a pair of jaws, an upper jaw 1, and a lower jaw 2, illustrated in FIG. 1 in the closed or working position. The upper and lower jaws are provided with curved pressure plates 3 and 4, respectively.

The curved pressure plates are made of 1/16" aluminum plate and are large enough to accommodate 5"–6" sphygmomanometer cuffs. The plates are rigidly fastened to the jaws by mechanical fasteners 17.

The lower jaw is made from a single thickness of ¼" aluminum plate the perimeter of which includes a section where several ratchet teeth 2a have been cut. A pair of connector plates 6 are rigidly fastened to upper jaw 1 by mechanical fasteners such as nuts and bolts 7. Spacers (not shown) are provided in association with the fasteners 7 between the connector plates 6 to retain the upper jaw 1 therebetween. One of the bolts passes through a stainless steel bushing 8 and serves not only to hold the assembly together, but also as a pivot about which a pawl 5 can rotate. To ensure a freely moving pawl, the length of the bushing is specified to be 0.004" to 0.005" greater than the thickness of the aluminum plate from which the pawl is made. The pawl 5 includes a finger 5a which engages ratchet teeth 2a to prevent jaws 1 and 2 from opening until released. The finger 5a is forced against the ratchet teeth 2a by a spring 9. The spring 9 is anchored at the point A where the end of the spring enters a hole in one of the connector plates 6. From the anchor point A the spring is wrapped around a stud 10 and then bears against the upper portion of the pawl to force the finger 5a against the teeth 2a.

Pivot means in the form of an axle 11 passes through connector plates 6, lower jaw 2 and finally through upper jaw 1 to permit relative movement of jaws 1 and 2 in the direction B and C, respectively. A locking washer/nut arrangement 12, 13 holds the axle 11 in position. The ratchet and pawl combination prevents either jaw from reversing direction holding the pressure plates 3 and 4 firmly in a working position. The pawl 5 includes a release lever 5b which extends from between connector plates 6 beyond the upper jaw. The clamping device is released by exerting a pressure in direction D on the lever which results in the disengagement of the finger 5a from the teeth 2a. Thus, a reliable releasable locking means is provided.

In use, as illustrated in FIG. 2, the clamping device according to the invention serves to hold the cuff of a sphygmomanometer firmly against the upper arm of a patient not directly accessible by virtue of the patient being enclosed in a casualty bag, to permit the determination of the patient's blood pressure. Specifically, the sphygmomanometer cuff (not shown) is folded and placed over the patient's arm in the approximate vicinity of the brachial artery and the clamping device according to the invention secures the cuff in place. When the clamp is closed over the cuff, the arm is virtually surrounded, the clamping device gripping both the cuff and the patient's arm. The sphygmomanometer 20 functions in a typical manner. The Korotkow sounds are detected with an electronic stethoscope 22, because the pulses must be detected through at least one layer of material, and systolic and diastolic pressures are read off the manometer 20.

TESTING THE DEVICE

Blood pressure was measured on each of 10 subjects under three different conditions with an approximate 10 minute interval between each measurement. The first measurement was made with the person in a casualty handling bag followed by a measurement while he was in a heavy overgarment and finally a measurement on the bare arm as would be done under normal conditions. This sequence was chosen to assure an unbiased casulty bag reading. Each test was done with a regular adult cuff and also a large adult cuff to ascertain the advantages or disadvantages of one over the other. The tests were performed as follows:

Casulty bag

The subject was placed in a casualty handling bag in a supine position on a recovery stretcher and the unit was closed up. The man was then moved inside the bag so that he was as close possible to one side of the bag. This would leave more slack on the opposite side which would allow better access to the arm on which the measurement was to be taken. The arm was extended down the side with the palm facing upward.

Before applying the clamp, the pressure cuff was folded twice to form a pad approximately 5"×5" with the inflation tubing on one external side (large adult cuff=5"×6").

The clamp was then applied to the upper arm such that the larger, fixed support was cradling the outer portion of the arm and the smaller, movable pad was positioned over the inner arm. The folded pressure cuff was then placed over the brachial artery and under the movable pad of the clamp with the bulb and manometer tubing on the portion against the arm. The clamp was then closed to secure the cuff against the arm. The tubing was connected to the manometer which was placed alongside and tilted to make readings more readily visible. The transducer of the electronic stethoscope was placed over the artery at the antecubital fossa. A small, loose sand bag (6"×6"×2" approximately) was placed over the transducer. This bag served to hold the tranducer firmly in place. It also insulted the unit from external sounds and prevented movement artifacts which were present when it was held by hand.

The electronic stethoscope was turned on and the cuff was inflated to a pressure reading midway between the expected systolic/diastolic reading and a quick check was made for an audible arterial sound and the position of the transducer was adjusted as necessary. The pressure was increased to approximately 180 mm and then released to ascertain the systolic and diastolic readings after which the cuff was released and removed. After a 10 minute period, the above procedure was repeated with the large adult pressure cuff.

Heavy Overgarment

The subject was clothed in a heavy overgarment and placed in a supine position on a recovery stretcher. The pressure cuff was wrapped around the covered arm in a normal fashion and the arm was extended along the body with the palm up. The transducer was placed over the artery at the antecubital fossa and covered with the sand bag. The same procedure as outlined under the previous test was followed to properly position the transducer and the blood pressure was read. After repeating the test with the larger cuff, the subject removed the overgarment.

Normal bare arm

The subject assumed a supine position on the stretcher with the arm extended, palm up, along the body. The pressure cuff and transducer were applied in a normal fashion on the bare arm. The method used in the above test was followed using both pressure cuffs.

The results were tabulated in Table I showing the readings using the adult cuff and the large adult cuff on a person in a casualty handling bag, in a heavy overgarment and under normal conditions.

TABLE I

| | BLOOD PRESSURE MEASUREMENTS | | | | | |
|---|---|---|---|---|---|---|
| | Through Bag | | Through CW Suit | | Bare Arm | |
| Subject | Reg Cuff | Lge Cuff | Reg Cuff | Lge Cuff | Reg Cuff | Lge Cuff |
| 1 | 139/80 | 138/84 | 142/80 | 136/80 | 135/84 | — |
| 2 | 119/86 | 118/90 | 118/85 | 118/88 | 119/89 | — |
| 3 | 118/92 | 120/90 | 120/90 | 118/85 | 112/85 | — |
| 4 | 150/80 | 148/75 | 155/84 | 158/82 | 155/84 | — |
| 5 | 135/90 | 135/88 | 142/82 | 140/92 | 146/88 | — |
| 6 | 135/80 | 128/80 | 140/80 | 138/80 | 138/82 | — |
| 7 | 128/78 | 122/78 | 120/80 | 118/76 | 118/74 | — |
| 8 | 138/94 | 138/90 | 138/96 | 140/94 | 138/92 | — |
| 9 | 118/70 | 114/68 | 130/80 | 126/78 | 122/70 | — |
| 10 | 110/68 | 106/66 | 122/72 | 120/72 | 118/68 | — |

The results of the tests described above are shown in Table I. The measurements taken show that the blood pressure readings of a casualty can be replicated, within biological variations, through a casualty bag, a heavy overgarment and a bare arm. The results also show that there is virtually no difference between reading taken with a regular cuff and a large cuff. It should also be noted, that during the entire test sequence, difficulty in obtaining a blood pressure reading occurred only once. The clamp was not properly positioned on the patient's upper arm and the artery was not occluded. However, with a minor adjustment of the clamp position, a reading was easily obtained.

Although the clamping device has been described above in relation to the measurement of blood pressures through casualty bags, it should be obvious to a person skilled in the art that by using a conventional sphygmomanometer and electronic stethoscope together with the clamping device according to the invention, other examples of obtaining blood pressures in difficult scenarios can be overcome. For example, a situation may arise when a patient's clothing may not or can not be removed, e.g., heavy coveralls in a toxic environment, or a parka in a very cold environment, or a pressurized suit or diving suit which cannot be removed quickly. The mere bulk of the clothing may prohibit placing a sphymomanometer cuff around the arm and certainly the layers of clothing necessitate an electronic stethoscope for ausculation. Although thigh cuffs are avilable, they are not always at hand. A normal sized brachial cuff may not physically fit around the thigh, and although the normal cuff isn't wide enough for an accurate femoral blood pressure, it is contemplated that the clamping device according to the invention can adapt it to the thigh for a ball park reading. In more remote examples when both arms are in slings, or in splints, or are splinted to the body, and a brachial blood pressure is desired, the clamping device according to the invention could make it possible to obtain a blood pressure reading.

The embodiments of the invention in which an exclusive property or privilege is claimed are defined as follows:

1. A device to enable the determination of a blood pressure reading with a sphygmomanometer on a patient whose upper arm is not directly accessible, comprising
a pair of jaws;

pivot means to permit relative pivotal movement of said pair of jaws;

releasable locking means associated with said pivot means to lock said pair of jaws in a working position; a plate fastened to each side of one jaw of said pair of jaws, said one jaw and said locking means being between the plates; and a curved pressure plate carried by each jaw of said pair of jaws, to provide opposed concave surfaces which are sufficiently large to accommodate a folded sphygmomanometer cuff and a patient's upper arm, such that in operation said folded sphygmomanometer cuff is positioned against said upper arm in the area of the brachial artery by said curved pressure plates and the cuff is inflated to occlude the brachial artery to enable determination of the patient's blood pressure.

2. An apparatus for measuring the blood pressure of a patient whose arm is covered by heavy protective clothing or the like, comprising sphygmomanometer means including an inflatable cuff for placing against the patient's upper arm over said heavy clothing in the area of the brachial artery; electronic stethoscope means; and a device to be placed over said inflatable cuff to firmly hold said cuff against the patient's arm, to enable the taking of a blood pressure reading, said device comprising a pair of jaws;

pivot means to permit relative pivotal movement of said pair of jaws;

releasable locking means associated with said pivot means to lock said pair of jaws in a working position; a plate fastened to each side of one jaw of said pair of jaws, said one jaw and said locking means being between the plates; and a curved pressure plate carried by each jaw of said pair of jaws to provide opposed concave surfaces which are suffiently large to accommodate a folded sphygmomnometer cuff and a patient's upper arm, such that in operation said folded sphygmomnometer cuff is positioned against said upper arm in the area of the brachial artery by said curved pressure plates and the cuff is inflated to occlude the brachial artery to enable determination of the patient's blood pressure.

3. A clamping device according to claim 1 or claim 2 wherein the releasable locking means is a ratcher/pawl combination.

* * * * *